United States Patent
Tang et al.

(10) Patent No.: US 8,780,344 B2
(45) Date of Patent: Jul. 15, 2014

(54) WAVEGUIDES CONFIGURED WITH ARRAYS OF FEATURES FOR PERFORMING RAMAN SPECTROSCOPY

(75) Inventors: Jing Tang, Menlo Park, CA (US); Wei Wu, Palo Alto, CA (US); Qiangfei Xia, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 0 days.

(21) Appl. No.: 13/384,862

(22) PCT Filed: Oct. 1, 2009

(86) PCT No.: PCT/US2009/059219
§ 371 (c)(1),
(2), (4) Date: Jan. 19, 2012

(87) PCT Pub. No.: WO2011/040923
PCT Pub. Date: Apr. 7, 2011

(65) Prior Publication Data
US 2012/0182550 A1    Jul. 19, 2012

(51) Int. Cl.
  *G01J 3/44*  (2006.01)
(52) U.S. Cl.
  USPC .......................................... 356/301

(58) Field of Classification Search
  USPC .............................................. 356/301, 72–73
  See application file for complete search history.

(56) References Cited

U.S. PATENT DOCUMENTS

| 6,777,244 | B2 | 8/2004 | Pepper |
| 7,224,451 | B2 | 5/2007 | Naya |
| 7,483,130 | B2 | 1/2009 | Baumberg |
| 2010/0085566 | A1* | 4/2010 | Cunningham ................ 356/301 |

FOREIGN PATENT DOCUMENTS

JP    2006349463    12/2006

* cited by examiner

*Primary Examiner* — Tarifur Chowdhury
*Assistant Examiner* — Abdullahi Nur

(57) ABSTRACT

Embodiments of the present invention are directed to systems for performing surface-enhanced Raman spectroscopy. In one embodiment, a system for performing Raman spectroscopy includes a waveguide layer configured with at least one array of features, and a material disposed on at least a portion of the features. Each array of features and the waveguide layer are configured to provide guided-mode resonance for at least one wavelength of electromagnetic radiation. The electromagnetic radiation produces enhanced Raman scattered light from analyte molecules located on or in proximity to the material.

16 Claims, 14 Drawing Sheets

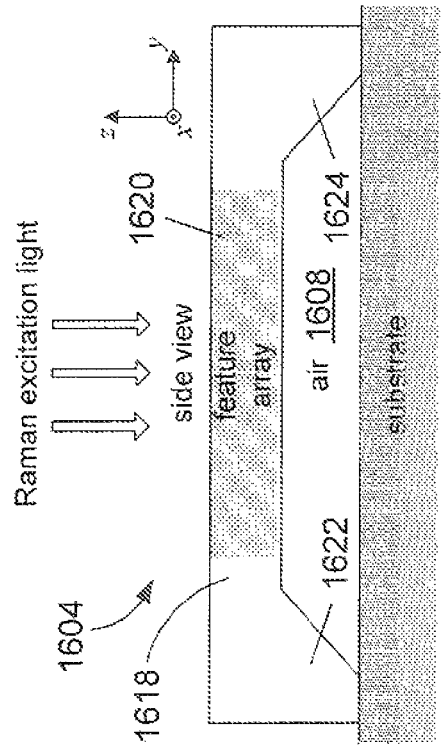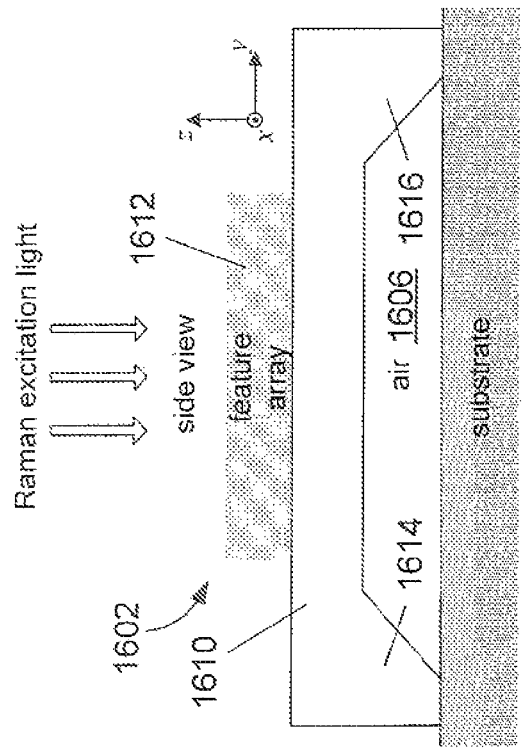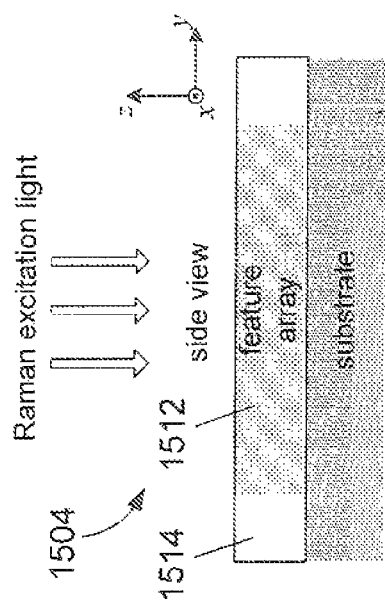
Figure 15A
Figure 15B
Figure 16A
Figure 16B

WAVEGUIDES CONFIGURED WITH ARRAYS OF FEATURES FOR PERFORMING RAMAN SPECTROSCOPY

STATEMENT OF GOVERNMENT INTEREST

This invention has been made with Government support under Contract No. HR0011-09-3-0002, awarded by the Defense Advanced Research Projects Agency. The government has certain rights in the invention.

TECHNICAL FIELD

Embodiments of the present invention relate generally to systems for performing surface-enhanced Raman spectroscopy.

BACKGROUND

Raman spectroscopy is a spectroscopic technique used in condensed matter physics and chemistry to study vibrational, rotational, and other low-frequency modes in molecular systems. In a Raman spectroscopic experiment, an approximately monochromatic beam of light of a particular wavelength range passes through a sample of molecules and a spectrum of scattered light is emitted. The spectrum of wavelengths emitted from the molecule is called a "Raman spectrum" and the emitted light is called "Raman scattered light." A Raman spectrum can reveal electronic, vibrational, and rotational energies levels of a molecule. Different molecules produce different Raman spectrums that can be used like a fingerprint to identify molecules and even determine the structure of molecules.

The Raman scattered light generated by a compound (or ion) adsorbed on or within a few nanometers of a structured metal surface can be $10^3$-$10^{14}$ times greater than the Raman scattered light generated by the same compound in solution or in the gas phase. This process of analyzing a compound is called surface-enhanced Raman spectroscopy ("SERS"). In recent years, SERS has emerged as a routine and powerful tool for investigating molecular structures and characterizing interfacial and thin-film systems, and even enables single-molecule detection. Engineers, physicists, and chemists continue to seek improvements in systems and methods for performing SERS.

BRIEF DESCRIPTION OF THE DRAWINGS

FIGS. 15A-15B show side views of two Raman-active systems disposed on a substrate and operated in accordance with embodiments of the present invention.

FIGS. 16A-16B show side views of two Raman-active systems configured with air cladding regions and operated in accordance with embodiments of the present invention.

DETAILED DESCRIPTION

Embodiments of the present invention are directed to systems for performing surface-enhanced Raman spectroscopy. The systems include a waveguide configured with an array of features to support guided-mode resonance for certain wavelengths of Raman-excitation light which increases the intensity of the electromagnetic field associated with the Raman-excitation light. In particular, wavelengths of the Raman-excitation light can be selected to generate a spectrum of Raman scattered light associated with particular analyte molecules, and the waveguide and array of features can be configured to provide guided-mode resonance for the Raman-excitation light. Portions of the outer surfaces of the array of features are coated with a Raman-active material that when exposed to the Raman-excitation light cause analyte molecules located on, or in close proximity to, the Raman-active material to enhance the intensity of the Raman-scattered light.

The term "light" as used to describe the operation of system embodiments of the present invention is not intended to be limited to electromagnetic radiation with wavelengths that lie only within the visible portion of the electromagnetic spectrum, but is intended to also include electromagnetic radiation with wavelengths outside the visible portion, such as the infrared and ultraviolet portions of the electromagnetic spectrum, and can be used to refer to both classical and quantum electromagnetic radiation.

Figure 1:
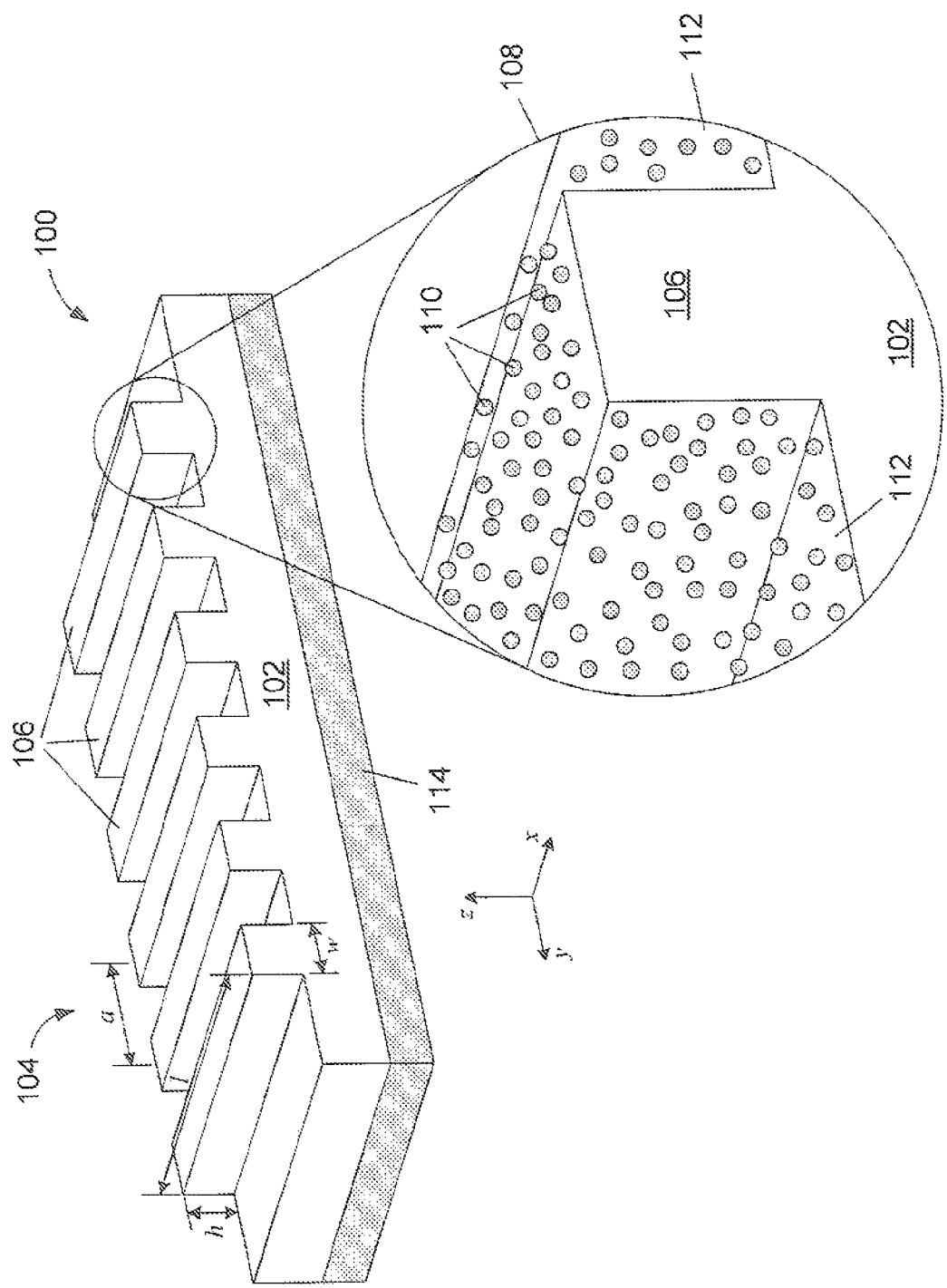
FIGS. 1-12 show isometric views of twelve different Raman-active systems, each system configured with a different array of features in accordance with embodiments of the present invention.

FIG. 1 shows an isometric view of a Raman-active system 100 configured in accordance with embodiments of the present invention. The Raman-active system 100 includes a waveguide layer 102 and an array of features 104 protruding from the waveguide layer 102 and formed from waveguide layer material. The array of features 104 is composed of features 106 that are approximately regularly-spaced with rectangular-shaped cross-sections. The features 106 form a one-dimensional lattice above the waveguide layer 102 with an approximately constant lattice spacing a in the y-direction. As shown in the example of FIG. 1, the length l of the features 106 substantially matches the width of the waveguide layer 102, and the height h and width w of each feature 106 and lattice constant a can be selected to support guided-mode resonance for wavelengths of Raman-excitation light injected into the waveguide layer 102.

In certain embodiments, the outer surface of the Raman-active system 100 can be coated with a Raman-active material in the form of Raman-active nanoparticles. In the example of FIG. 1, a portion of a rectangular feature 106 is magnified in an enlargement 108 revealing Raman-active nanoparticles 110 disposed on the outer surfaces of the features 106 and on the outer surface 112 of the waveguide layer 102. In other embodiments, the Raman-active material can be deposited as a thin Raman-active layer coating at least a portion of the outer surface of the rectangular features 106 and at least a portion of the surface of the waveguide layer 102 surrounding the features 106.

In certain embodiments, the waveguide layer 102 can be disposed on a surface of a substrate 114. The substrate 114 can be composed of a material having a lower refractive index than the waveguide layer material and serve as a cladding layer for the waveguide layer 102. In other embodiments, the substrate 114 can be eliminated with an air cladding surrounding the waveguide layer 102 and the features 106.

Figure 2:
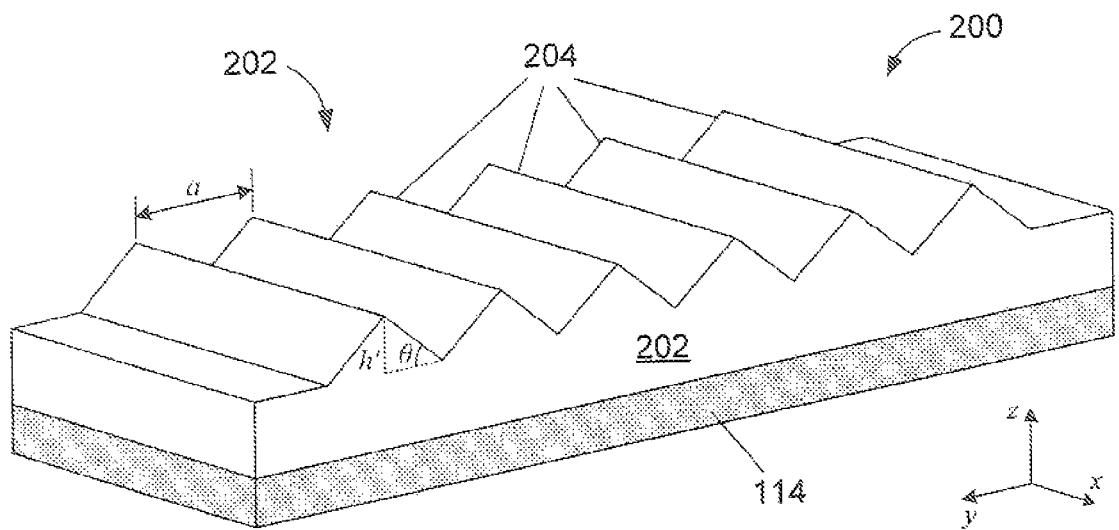

FIG. 2 shows an isometric view of a Raman-active system 200 configured in accordance with embodiments of the present invention. The Raman-active system 200 is nearly identical to the Raman-active system 100. In particular, the Raman-active system 200 includes the same waveguide layer 102, but the array of features 202 is composed of approximately regularly-spaced, saw-tooth-shaped features 204 protruding from the waveguide layer 102. The features 204 also form a one-dimensional lattice above the waveguide layer 102 with an approximately constant lattice spacing a in the y-direction Although magnification of the features 204 is not provided in FIG. 2, in certain embodiments, the outer surface of the Raman-active system 200 can be coated with a Raman-active material in the form of Raman-active nanoparticles, as described above with reference to the Raman-active system 100. In other embodiments, the Raman-active material can be deposited as a thin Raman-active layer coating the outer surface of the saw-toothed features 204.

Figure 3:
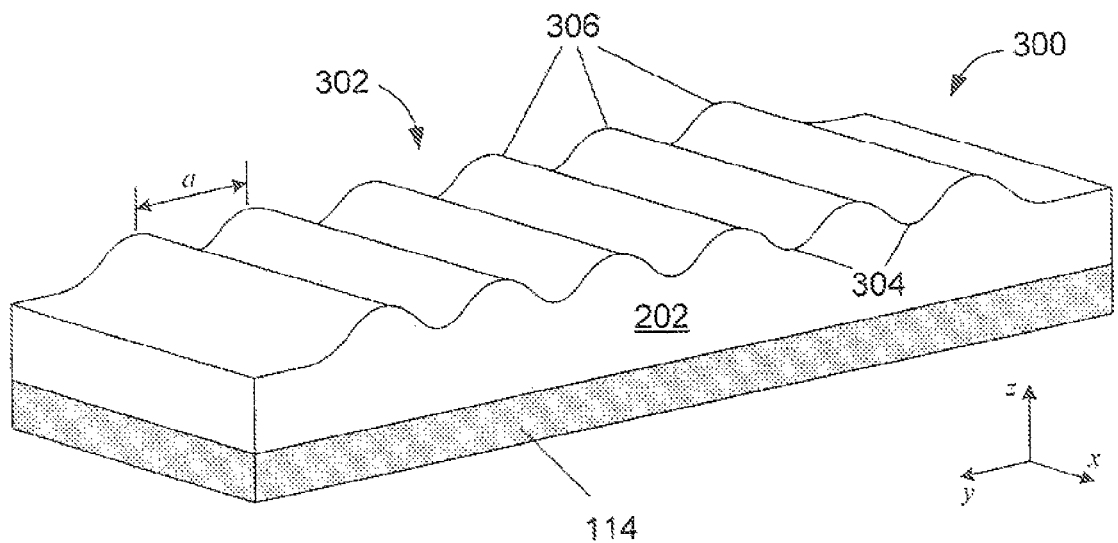

FIG. 3 shows an isometric view of a Raman-active system 300 configured in accordance with embodiments of the present invention. The Raman-active system 300 is also nearly identical to the Raman-active system 100. In particular, the Raman-active system 300 includes the same waveguide layer 102, but the array of features 302 is composed of a one-dimensional sinusoidal, or wave-like, pattern of alternating troughs 304 and ridges 306 protruding from the waveguide layer 102 and repeating in the y-direction with an approximately constant lattice spacing a. Although magnification of the array of features 302 is not provided in FIG. 3, in certain embodiments, the outer surface of the Raman-active system 300 can be coated with a Raman-active material in the form of Raman-active nanoparticles, as described above with reference to the Raman-active system 100. In other embodiments, the Raman-active material can be deposited as a thin Raman-active layer coating the outer surface of the array of features 302.

Figure 4:
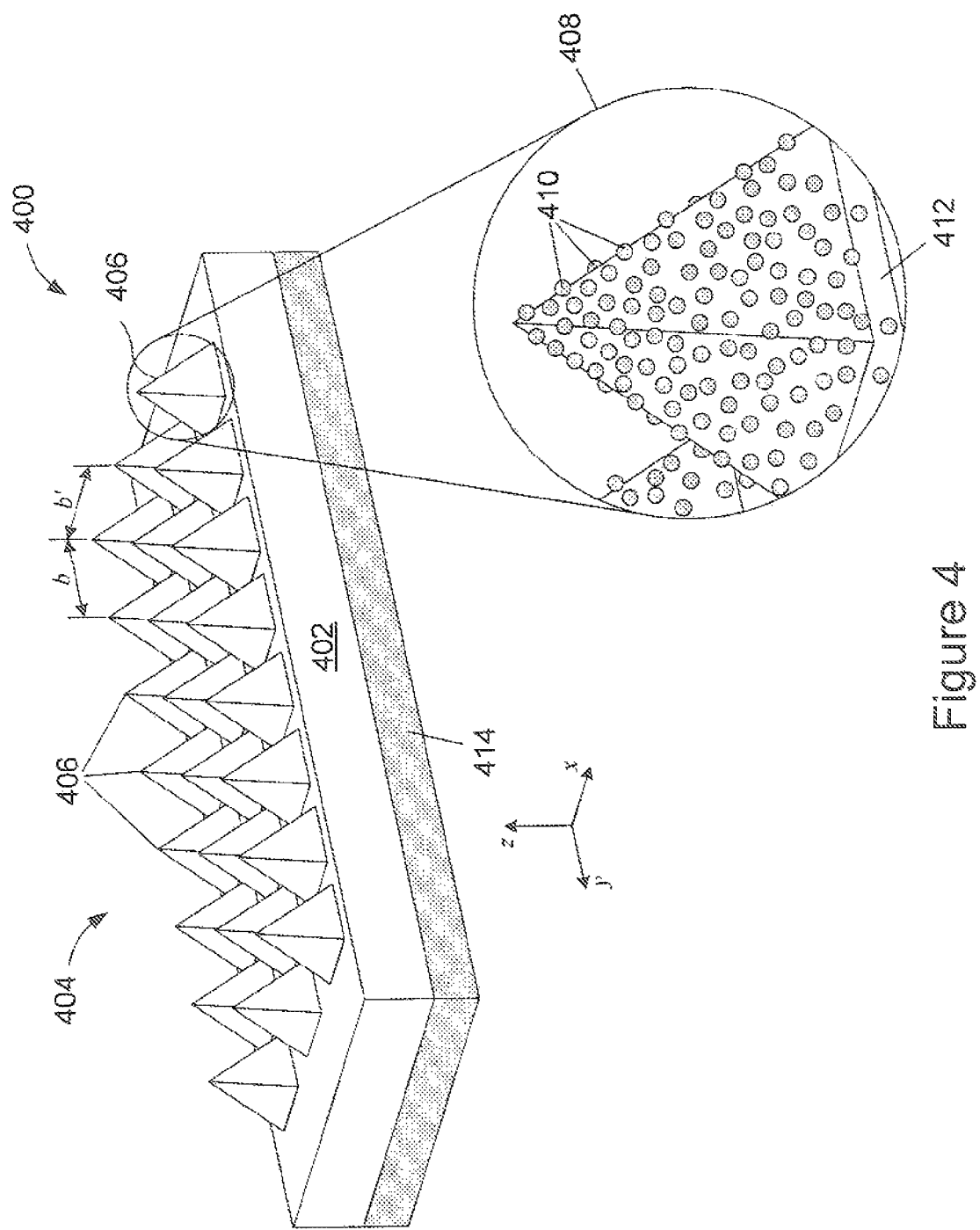

Embodiments of the present invention are not limited to one-dimensional arrays of features with between five and six features. The one-dimensional arrays of features can be composed of any suitable number of features protruding from the waveguide layer and extending in the y-direction. Embodiments of the present invention are not limited to one-dimensional array configurations described above with reference to FIGS. 1-3. In other embodiments, the array pattern can also be extended into the x-direction. FIG. 4 shows an isometric view of a Raman-active system 400 configured in accordance with embodiments of the present invention. The Raman-active system 400 includes a waveguide layer 402 and an array of features 404 protruding from the waveguide layer 402 and formed from waveguide layer material. The array of features 404 is composed of approximately regularly-spaced, pyramid-shaped features 406. The features 406 form a two-dimensional array 404 protruding from the waveguide layer 402 with an approximately constant lattice spacing b in the y-direction and an approximately constant lattice spacing b' in the x-direction. The feature 406 lattice constants b and b' and height and base dimensions can be selected to support guided-mode resonance for various Raman-excitation light wavelengths.

In certain embodiments, the outer surface of the Raman-active system 400 can be coated with a Raman-active material in the form of Raman-active nanoparticles. In the example of FIG. 4, a portion of a pyramid-shaped feature 406 is magnified in an enlargement 408 revealing Raman-active nanoparticles 410 disposed on the outer surfaces of the feature 406 and on the outer surface 412 of the waveguide layer 402. In other embodiments, the Raman-active material can be deposited as a thin Raman-active layer coating at least a portion of the outer surfaces of the pyramid-like features 406 and at least a portion the surface of the waveguide layer 402 surrounding the features 406.

In certain embodiments, as shown in FIG. 4, the waveguide layer 402 can be disposed on a surface of a substrate 414. The substrate 414 can be composed of a material having a lower refractive index than the waveguide layer material and serve as a cladding layer for the waveguide layer 402. In other embodiments, the substrate 414 can be eliminated with an air cladding surrounding the waveguide layer 402 and the features 406.

Figure 5:
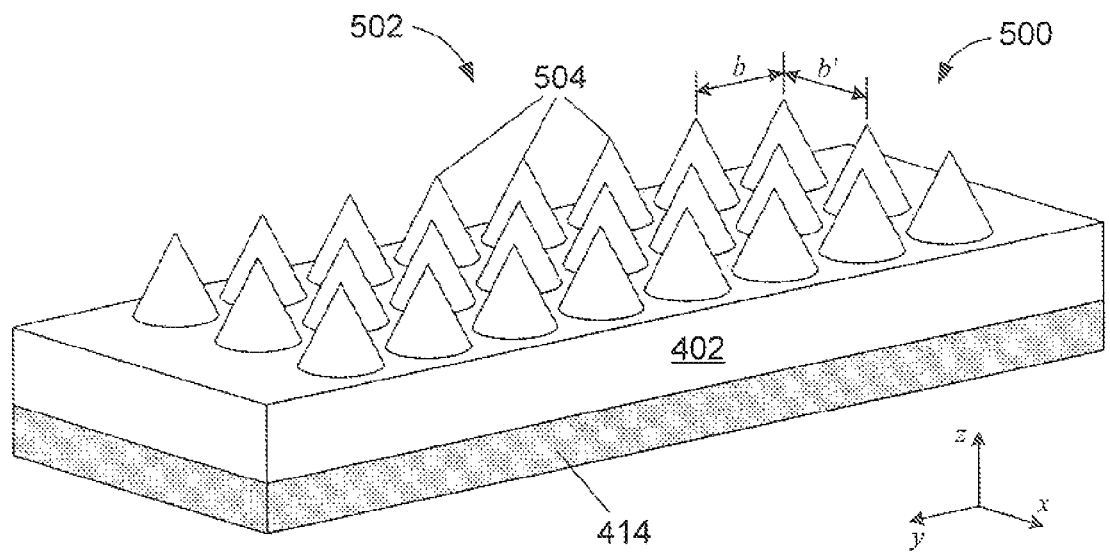

In other embodiments, the pyramid-shaped features of the Raman-active system 400 can be replaced by cone-shaped features. FIG. 5 shows an isometric view of a Raman-active system 500 configured in accordance with embodiments of the present invention. The Raman-active system 500 is nearly identical to the Raman-active system 400 except the array of features 502 of the Raman-active system 500 is composed of a two-dimensional array of cone-shaped features 504 protruding from the waveguide layer with an approximately constant lattice spacing b in the y-direction and an approximately constant lattice spacing b' in the x-direction.

Figure 6:
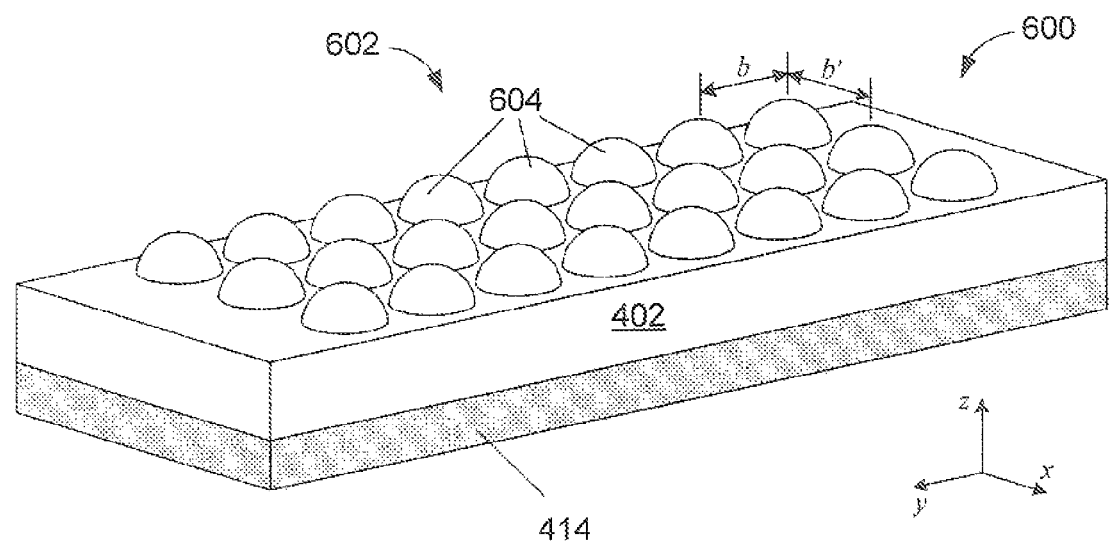

In other embodiments, the pyramid-shaped features of the Raman-active system 400 can be replaced by hemispherical-shaped features. FIG. 6 shows an isometric view of a Raman-active system 600 configured in accordance with embodiments of the present invention. The Raman-active system 600 is nearly identical to the Raman-active system 400 except the array of features 602 of the Raman-active system 600 is composed of a two-dimensional array of hemispherical-shaped features 604 protruding from the waveguide layer with an approximately constant lattice spacing b in the y-direction and an approximately constant lattice spacing b' in the x-direction.

Embodiments of the present invention are not limited to three rows of features extending in the y-direction along the length of the waveguide layer. In other embodiments, the number of rows extending along the length of the waveguide layer can range from as few as one row to two, four, or more rows of features. The number of features in each row of features extending in the x-direction can range from two to any suitable number of features. In other embodiments, the features forming a two-dimensional array of features can be configured with rectangular, square, cylindrical, elliptical, or any other suitably shaped xy-plane cross-section.

Figure 7:
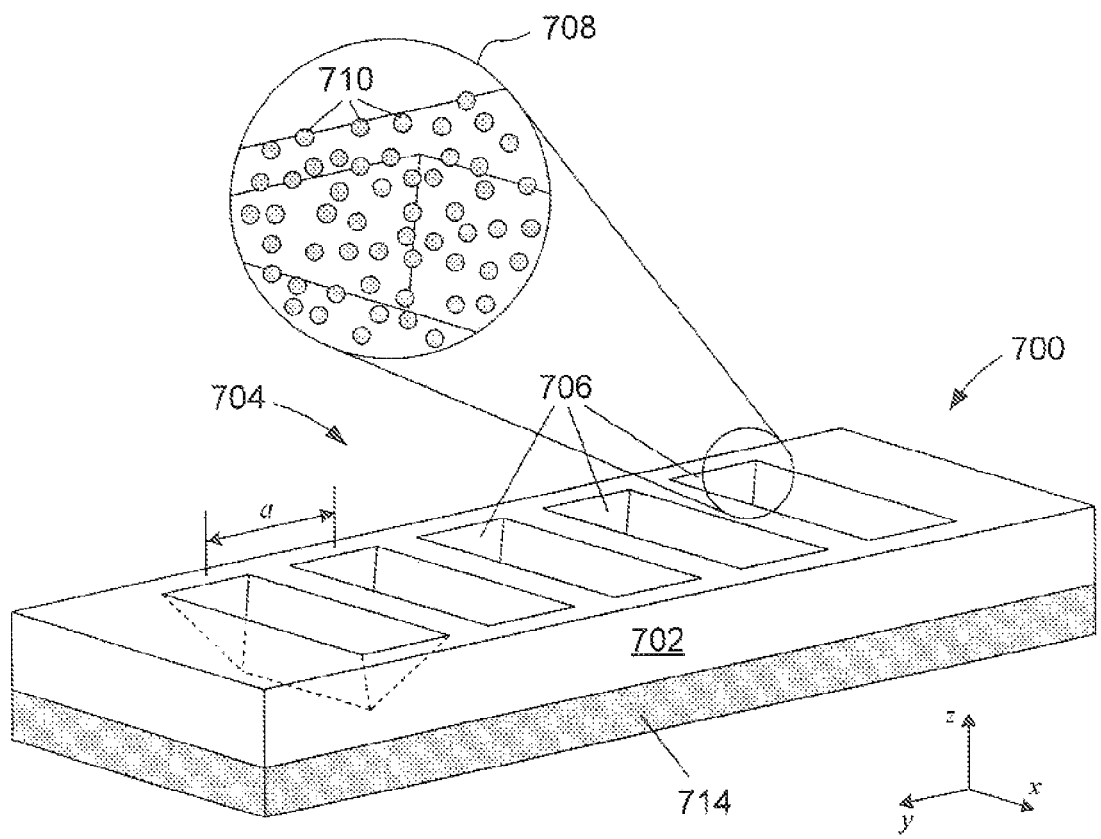

In still other embodiments, rather than the features of the array of features protruding from the waveguide layer, the array of features can be formed within the waveguide layer. FIG. 7 shows an isometric view of a Raman-active system 700 configured in accordance with embodiments of the present invention. The Raman-active system 700 includes a waveguide layer 702 and an array of features 704 formed within the waveguide layer 702. The array 704 is composed of approximately regularly-spaced, V-shaped trough features 706. The features 706 form a one-dimensional lattice within the waveguide layer 702 with an approximately constant lattice spacing a in the y-direction.

In certain embodiments, the outer surface of the Raman-active system 700 can be coated with a Raman-active material in the form of Raman-active nanoparticles. In the example of FIG. 7, a portion of a V-shaped feature 706 is magnified in an enlargement 708 revealing Raman-active nanoparticles 710 disposed on the outer surfaces of the features 706 and on the outer surface 712 of the waveguide layer 702. In other embodiments, the Raman-active material can be deposited as a thin Raman-active layer coating the outer surface of the V-shaped features 706 and the surface of the waveguide layer 702.

In certain embodiments, the waveguide layer 702 can be disposed on a surface of a substrate 714 composed of a material having a lower refractive index than the waveguide layer material and serves as a cladding layer for the waveguide layer 702. In other embodiments, the substrate 714 can be eliminated with an air cladding surrounding the waveguide layer 702.

Figure 8:
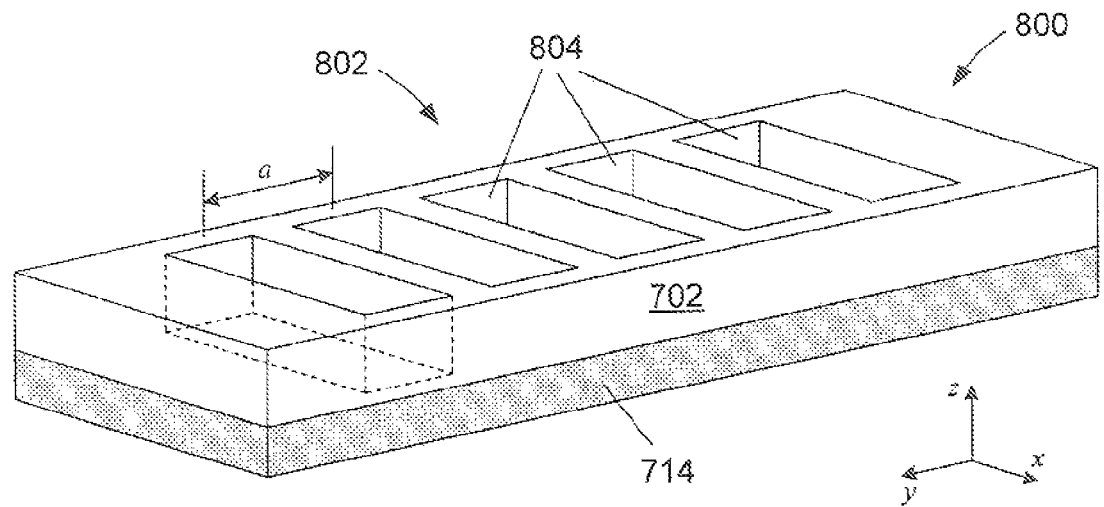

FIG. 8 shows an isometric view of a Raman-active system 800 configured in accordance with embodiments of the present invention. The Raman-active system 800 is nearly identical to the Raman-active system 700. In particular, the Raman-active system 800 includes the waveguide layer 702, but the features of the array of features 802 are approximately regularly-spaced, rectangular-shaped holes 804. The features 804 also form a one-dimensional lattice within the waveguide layer 702 with an approximately constant lattice spacing a in the y-direction. Although magnification of the features 804 is not provided in FIG. 8, in certain embodiments, the outer surface of the Raman-active system 800 can be coated with a Raman-active material in the form of Raman-active nanoparticles, as described above with reference to the Raman-active system 700. In other embodiments, the Raman-active material can be deposited as a thin Raman-active layer coating the outer surface of the features 804.

Figure 9:
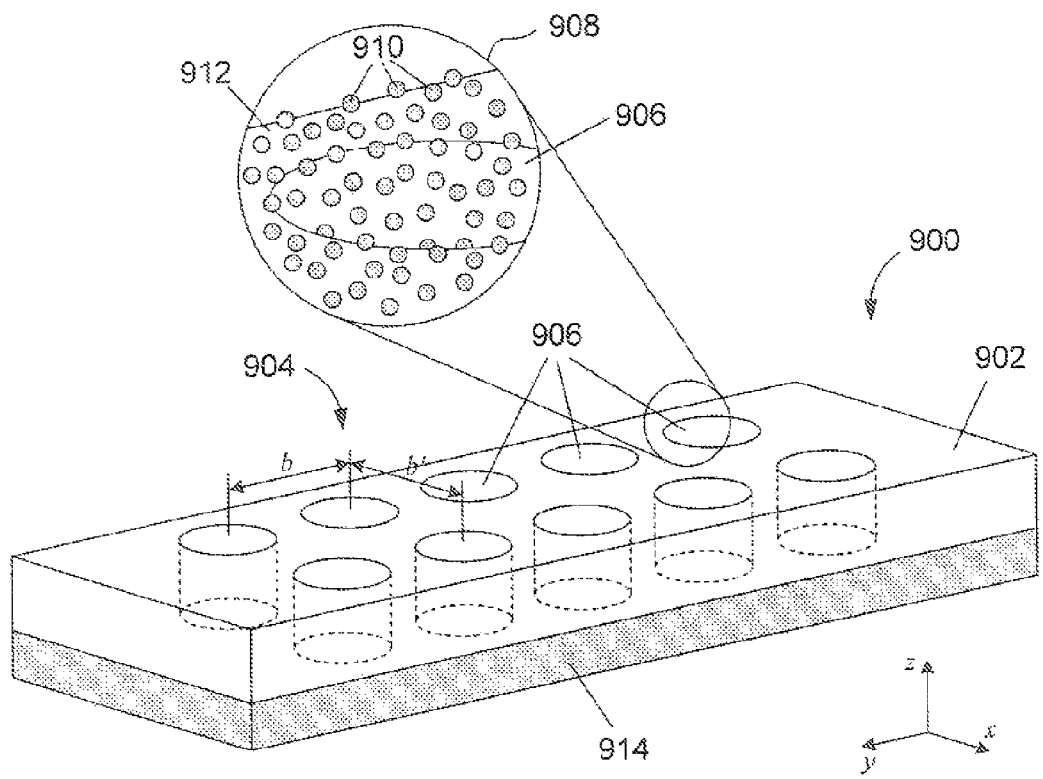

FIG. 9 shows an isometric view of a Raman-active system 900 configured in accordance with embodiments of the present invention. The Raman-active system 900 includes a waveguide layer 902 and an array of features 904 formed within the waveguide layer 902. The features of the array 904 are cylindrical-shaped holes 906. The features 906 form a two-dimensional feature lattice within the waveguide layer 902 with an approximately constant lattice spacing b in the y-direction and an approximately constant lattice spacing b' in they-direction.

In certain embodiments, the outer surface of the Raman-active system 900 can be coated with a Raman-active material in the form of Raman-active nanoparticles. In the example of FIG. 9, a portion of a feature 906 is magnified in an enlargement 908 revealing Raman-active nanoparticles 910 disposed on the outer surfaces of the features 906 and on the outer surface 912 of the waveguide layer 902. In other embodiments, the Raman-active material can be deposited as a thin Raman-active layer coating the outer surface of the features 906 and the surface of the waveguide layer 902.

As shown in the example of FIG. 9, in certain embodiments, the waveguide layer 902 can be disposed on a surface of a substrate 914 composed of a material having a lower refractive index than the waveguide layer material and serves as a cladding layer for the waveguide layer 902. In other embodiments, the substrate 914 can be eliminated with an air cladding surrounding the waveguide layer 902.

Figure 10:
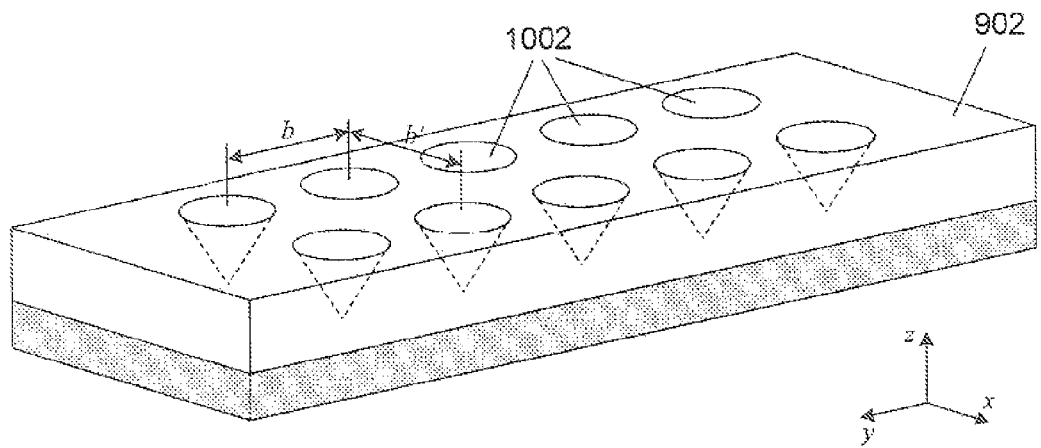
Figure 11:
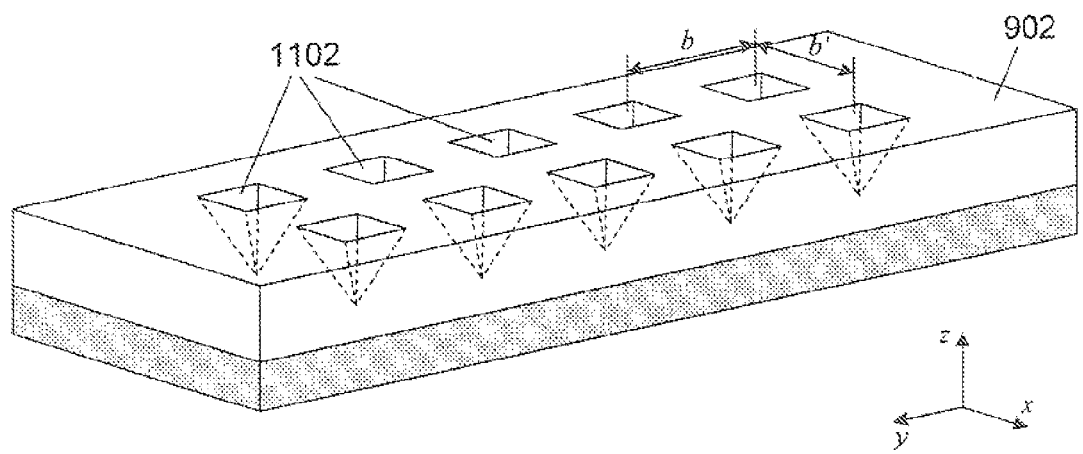
Figure 12:
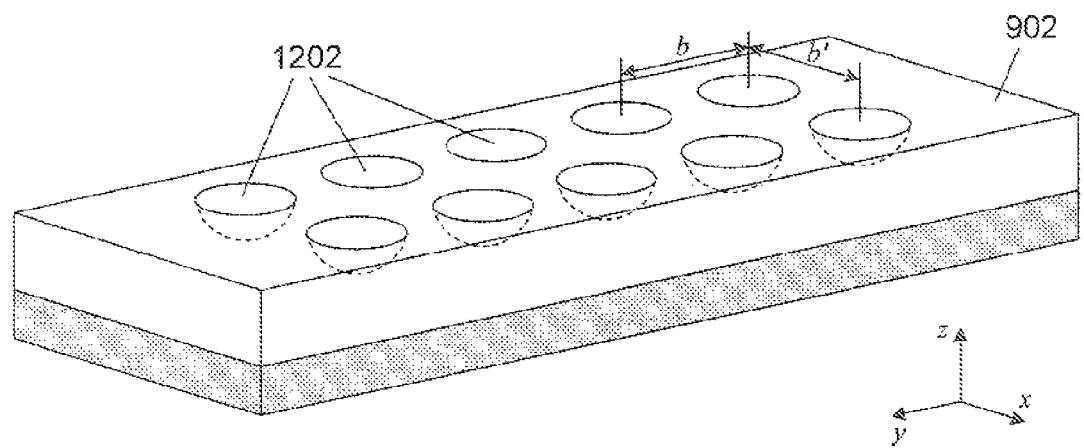

Embodiments of the present invention are not limited to features configured as cylindrical-shaped holes formed in the waveguide layer 902. In other embodiments, the features of the array can be inverted cone-shaped holes 1002, as shown in FIG. 10, the features of the array can be inverted pyramid-shaped holes 1102, as shown in FIG. 11, or the features of the array can be hemispherical-shaped holes or impressions 1202, as shown in FIG. 12.

In still other embodiments, the features can be square, rectangular, elliptical, or any other suitable-shaped hole formed in the waveguide layer. In other embodiments, the number of rows of features extending in the y-direction along the length of the waveguide layer can range from as few as one row to three or more rows of features. The number of features in each row of features extending in the x-direction can range from two to any suitable number of features.

Although FIGS. 1, 4, 7, and 9 show the Raman-active material disposed on the outer surface of the waveguide layers, in other embodiments the Raman-active material may be disposed only on the features. Guided-mode resonance enables the electromagnetic field associated with Raman-excitation light resonating within a waveguide layer to extend beyond the waveguide layer and interact with the Raman-active material disposed on the features. In other embodiments, the Raman-active systems may include a spacer layer composed of a dielectric material that separates the Raman-active material from the waveguide layer.

The waveguide layer of the Raman-active systems can be composed of an indirect elemental semiconductor, including silicon ("Si") and germanium ("Ge"), or Si based materials, such as glass, $SiO_x$ and $SiN_x$, or a compound semiconductor, including III-V materials, where Roman numerals III and V represent elements in the IIIa and Va columns of the Periodic Table of the Elements. Compound semiconductors can be composed of column IIIa elements, such as aluminum ("Al"), gallium ("Ga"), and indium ("In"), in combination with column Va elements, such as nitrogen ("N"), phosphorus ("P"), arsenic ("As"), and antimony ("Sb"). Compound semiconductors can also be further classified according to the relative quantities of III and V elements. For example, binary semiconductor compounds include GaAs, InP, InAs, and GaP; ternary compound semiconductors include $GaAs_yP_{1-y}$, where y ranges from greater than 0 to less than 1; and quaternary compound semiconductors include $In_xGa_{1-x}As_yP_{1-y}$, where both x and y independently range from greater than 0 to less than 1. Other types of suitable compound semiconductors include II-VI materials, where II and VI represent elements in the IIb and VIa columns of the periodic table. For example, CdSe, ZnSe, ZnS, and ZnO are examples of binary II-VI compound semiconductors.

The waveguide layer can also be composed of materials that are at least partially transparent to the wavelengths comprising the Raman-excitation light. For example, the waveguide layer can be composed of glass or a suitable polymer that transmits Raman excitation wavelengths in the visible portion of the electromagnetic spectrum. The waveguide layer can be composed of Si or a suitable polymer that transmits Raman-excitation wavelengths in the infrared portions of the electromagnetic spectrum. The waveguide layer can also be composed of quarts, glass, a polymer, or aluminum oxide ("$Al_2O_3$") that transmits Raman excitation wavelengths in the ultraviolent portion of the electromagnetic spectrum.

The Raman-active material comprising the Raman-active particles and Raman-active layers deposited on the array and surface of the waveguide layer can be composed of silver ("Ag"), gold ("Au"), copper ("Cu") or another metal suitable for forming a structured metal surface.

The substrate can be composed of a substantially transparent or non-transparent dielectric material, including glass, silicon dioxide ("SiO$_2$"), Al$_2$O$_3$, a transparent or non-transparent dielectric polymer, or any other suitable material for serving as cladding layer for the waveguide layer.

Figure 13:
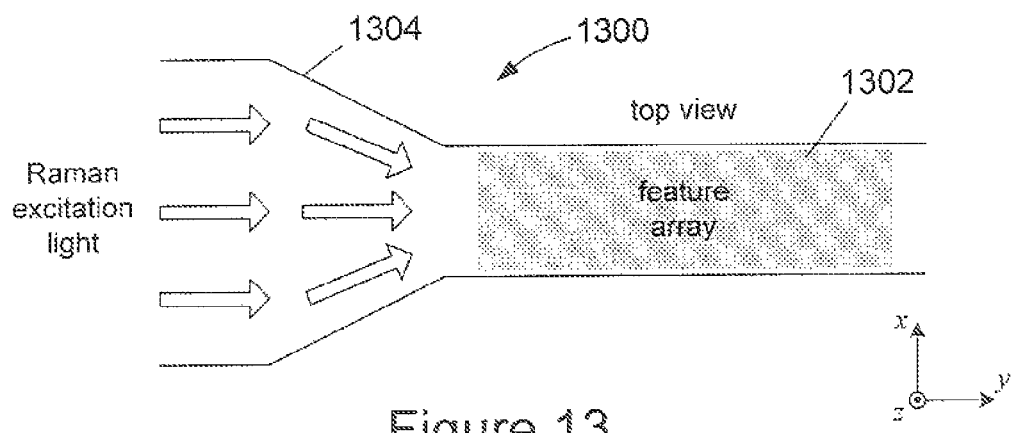
FIG. 13 shows a top view of a Raman-active system configured to channel Raman-excitation light into an array of features in accordance with embodiments of the present invention.

The waveguide layer can be configured to channel and concentrate Raman-excitation light into the region of the waveguide layer configured with the array of features. FIG. 13 shows a top view of a Raman-active system configured to channel Raman-excitation light into an array of features 1302 region of a waveguide layer 1300 in accordance with embodiments of the present invention. The array of features 1302 can be formed above the waveguide layer 1300, as described above with reference to FIGS. 1-6, or formed within the waveguide layer 1300, as described above with reference to FIG. 7-12. The waveguide layer 1300 can be disposed on a surface of a substrate (not shown) composed of a material with a relatively lower refractive index than the waveguide layer material. As shown in the example of FIG. 13, the waveguide layer 1300 includes an xy-plane tapered region 1304 that channels and concentrates Raman-excitation light into the array of features 1302 region of the waveguide layer 1300.

Figure 14A:
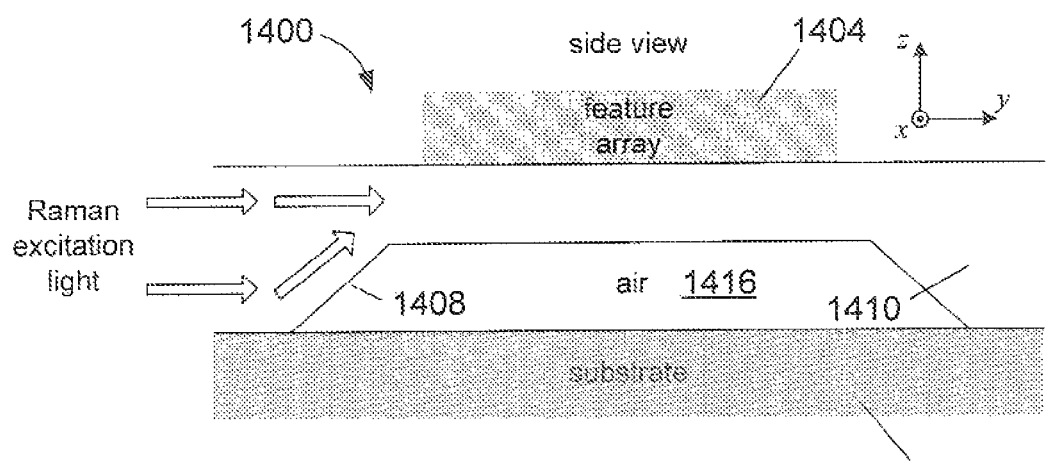
FIGS. 14A-14B show side views of two Raman-active systems configured to channel Raman-excitation light into corresponding array of features in accordance with embodiments of the present invention.
Figure 14B:
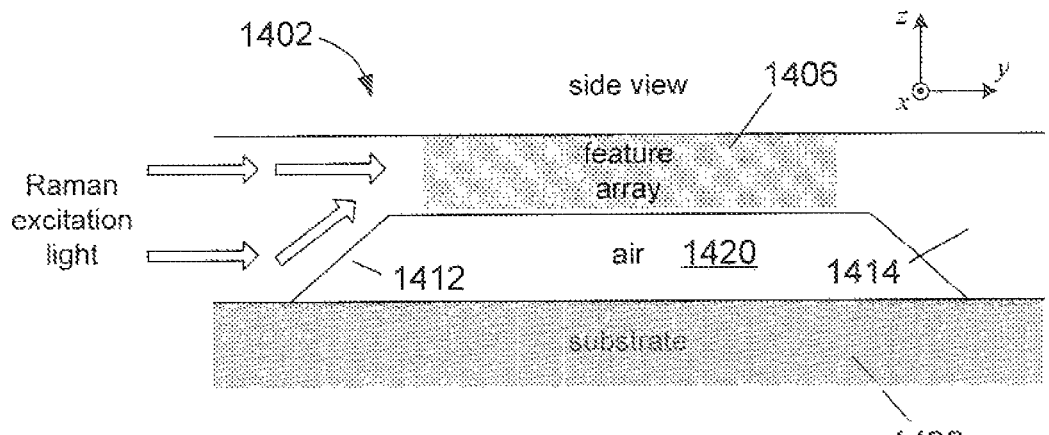

As described above, the various Raman-active systems can be implemented with an air cladding surrounding the waveguide layer. FIGS. 14A-14B show side views of two Raman-active systems configured to channel Raman-excitation light into corresponding arrays of features in accordance with embodiments of the present invention. In the example of FIG. 14A, a first array of features 1404 is formed above a first waveguide layer 1400, as described above with reference to FIGS. 1-6. In the example of FIG. 14B, a second array of features 1406 is formed within a second waveguide layer 1402, as described above with reference to FIGS. 7-12. As shown in the example of FIG. 14A, the waveguide layer 1400 includes tapered regions 1408 and 1410, and, in FIG. 14B, the waveguide layer 1402 includes tapered regions 1412 and 1414. The tapered region 1408 is configured to channel Raman-excitation light into the array of features 1404, and the tapered region 1412 also is configured to channel Raman-excitation light into the array of features 1406. Tapered regions 1408 and 1410 are configured to form an air cladding region 1416 between the array of features 1404 portion of the waveguide layer 1400 and a substrate 1418. Tapered regions 1412 and 1414 are configured to form an air cladding region 1420 between the array of features 1406 portion of the waveguide layer 1402 and a substrate 1422.

Embodiments of the present invention are not limited to introducing Raman-excitation light via the waveguide. In other embodiments, the arrays of features can be operated as diffraction gratings for capturing incident Raman-excitation light and establishing guided-mode resonance with Raman-excitation light within the waveguide.

FIGS. 15A-15B show side views of Raman-active systems 1502 and 1504 disposed on a substrate 1506 and operated in accordance with embodiments of the present invention. For the Raman-active system 1502, the array of features 1508 can be formed above a waveguide layer 1510, as described above with reference to FIGS. 1-6. For the Raman-active system 1504, an array of features 1512 can be formed within a waveguide layer 1514, as described above with reference to FIG. 7-12. As shown in the examples of FIGS. 15A-15B, Raman-excitation light is directed nearly perpendicular to the array of features 1508 and 1512 located in the xy-plane.

FIGS. 16A-16B show side views of Raman-active systems 1602 and 1604 configured with air cladding regions 1606 and 1608 and operated in accordance with embodiments of the present invention. The Raman-active system 1602 includes a waveguide layer 1610 with an array of features 1612 formed above the waveguide, as described above with reference to FIGS. 1-6, and tapered regions 1614 and 1616 forming air cladding region 1606. The Raman-active system 1604 includes a waveguide layer 1618 with an array of features 1620 formed within the waveguide, as described above with reference to FIGS. 7-12, and tapered regions 1622 and 1624 forming air cladding region 1608. As shown in the examples of FIGS. 16A-16B, Raman-excitation light is directed nearly perpendicular to the arrays of features 1612 and 1620 located in the xy-plane.

Note that Raman-excitation light is not limited to, normal incidence with the xy-plane of the array of feature, as represented in FIGS. 15 and 16. Raman-excitation light can be incident from any suitable angle.

The Raman-active systems described above with reference to FIGS. 1-16 can be implemented in analyte sensors that are used to identify one or more analyte molecules by configuring the waveguide layer with an array of features that supports guided-mode resonance of appropriate wavelengths of the Raman-excitation light selected to stimulate emission of Raman scattered light from analyte molecules disposed on, or located in close proximity to, the features of the array of features. The Raman-active material disposed on the features of the array of features intensify the Raman scattered light when illuminated by appropriate Raman excitation wavelengths. The Raman scattered light can be detected to produce a Raman spectrum that can be used like a finger print to identify the analyte.

Figure 17A:
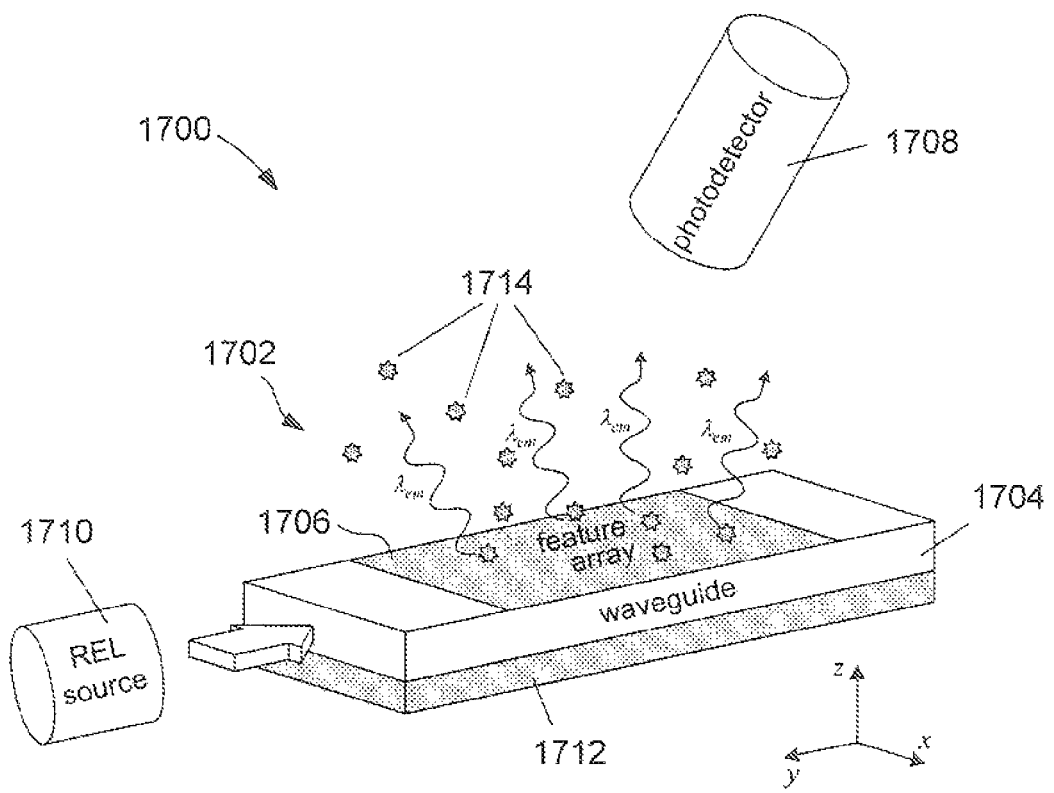
FIGS. 17A-17B show schematic representations of exemplary analyte sensors configured and operated in accordance with embodiments of the present invention.
Figure 17B:
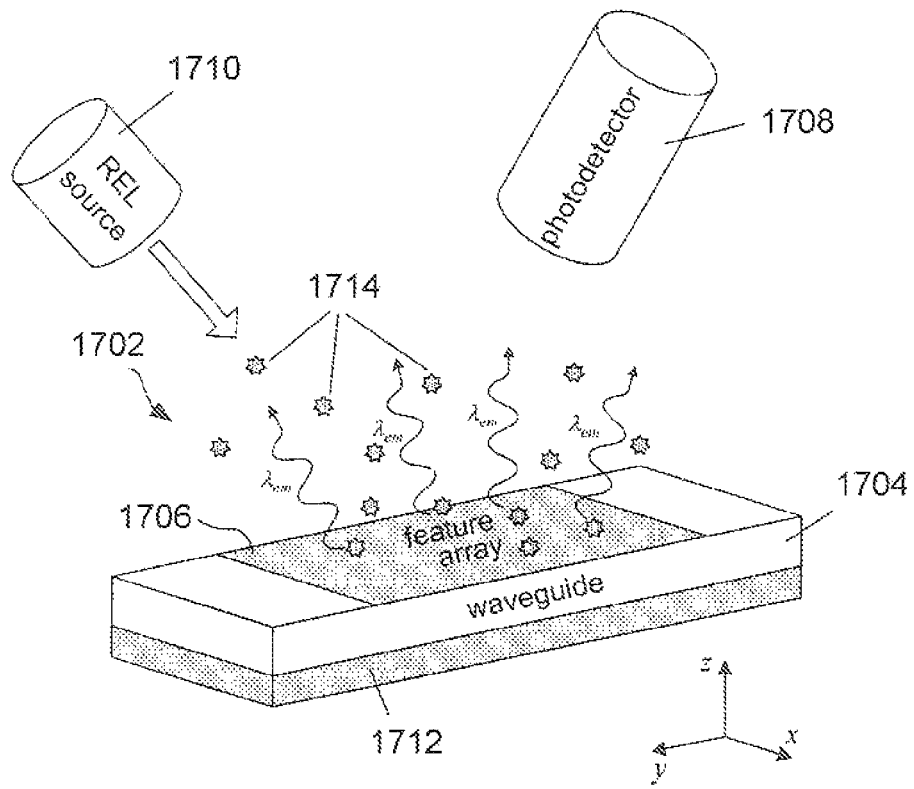

FIGS. 17A-17B show schematic representations of analyte sensors configured and operated in accordance with embodiments of the present invention. Analyte sensor 1700 includes a Raman-active system 1702 composed of a waveguide layer 1704 and an array of features 1706, as described above with reference to FIGS. 1-12, a photodetector 1708, and a Ramen-excitation light source 1710. The Raman-active system includes a substrate 1712 that serves as a cladding layer, but in other embodiments, the waveguide layer 1704 can be configured with an air cladding region, as described above with reference to FIGS. 14 and 16. In the example shown in FIG. 17A, the light source 1710 injects Raman-excitation light into the waveguide layer 1704. In the example shown in FIG. 17B, the light source 1710 is positioned so that Raman-excitation light is incident directly on the array of features 1706, rather than injecting the Raman-excitation light into the waveguide layer 1704. The photodetector 1708 is positioned to capture at least a portion of the Raman scattered light emitted by an analyte 1714 located in close proximity to the array of features 1704.

The array of features 1706 is configured to support guided-mode resonance with certain wavelengths of Raman-excitation light. Guided-mode resonance enhances, or increases, the intensity of the associated electromagnetic field. For example, when the wavelength of Raman-excitation light is resonant with an array of features, the electromagnetic field associated with the Raman-excitation light builds or is enhanced by guided-mode resonance within the waveguide. As a result, Raman-excitation light can be emitted or coupled out through the features and waveguide to interact with analyte molecules and cause emission of Raman scattered light from the analyte molecules located in close proximity to the features. The enhanced electromagnetic field also interacts with the Raman-active material to further enhance this emission process for analyte molecules located on, or in close proximity to, the Raman-active material.

Figure 18:
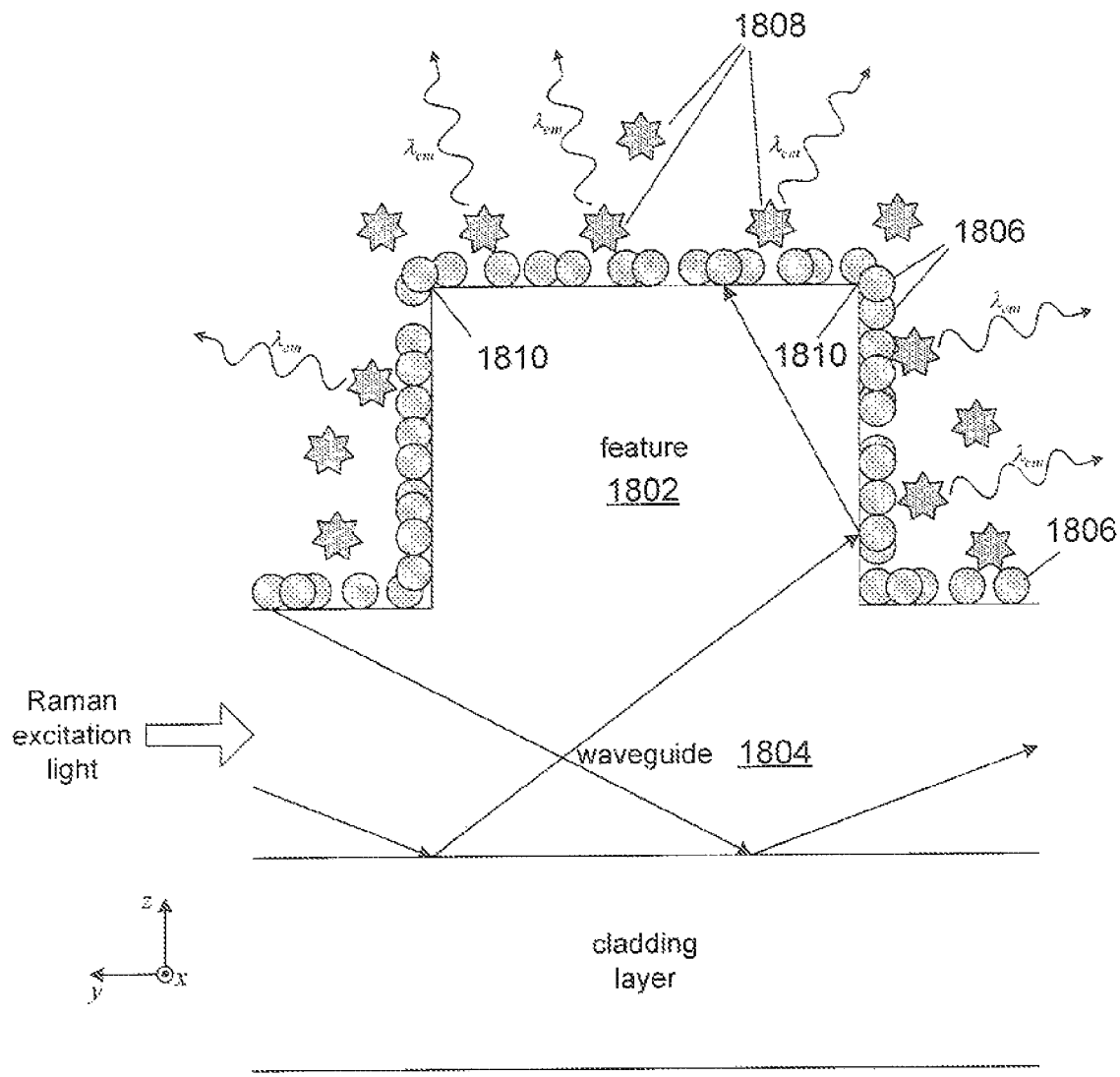
FIG. 18 shows an enlarged cross-sectional view of an exemplary rectangular feature configured and operated in accordance with embodiments of the present invention.

FIG. 18 shows an enlarged cross-sectional view of an exemplary rectangular feature 1802 formed above a waveguide layer 1804 of a Raman-active system configured as described above with reference to FIG. 1. As shown in the example of FIG. 18, the feature 1802 is coated with Raman-active nanoparticles 1806 located on the outer surface of the feature 1802 and on the outer surface of the waveguide layer 1804. An analyte 1808 is introduced and Raman-excitation light of a suitable wavelength for establishing guided-mode resonance and for generating Raman scattered light from the analyte 1808 is injected into the waveguide layer 1804. As a result, the intensity of the electromagnetic field associated with the Raman-excitation light increases, and the Raman-excitation light is output from the feature 1802 with the strongest output intensity occurring near the feature edges and corners, such as corners 1810. The wavelengths selected for the Raman-excitation light cause the analyte 1808 located near the feature 1802 or the waveguide layer 1804 to emit a Raman spectrum of Raman scattered light over a range of wavelengths denoted by $\lambda_{em}$. The intensity of the Raman scattered light may also be enhanced as a result of two mechanisms associated with the Raman-active material. The first mechanism is an enhanced electromagnetic field produced at the surface of the Raman-active nanoparticles 1806. As a result, conduction electrons in the metal surfaces of the nanoparticles 1806 are excited into an extended surface excited electronic state called a "surface plasmon polariton." Analytes 1808 adsorbed on or in close proximity to the nanoparticles 1806 experience a relatively strong electromagnetic field. Molecular vibrational modes directed normal to the nanoparticle 1806 surfaces are most strongly enhanced. The intensity of the surface plasmon polariton resonance depends on many factors including the wavelengths of the Raman excitation light. The second mode of enhancement, charge transfer, may occur as a result of the formation of a charge-transfer complex between the surfaces of the nanoparticles 1806 and the analyte 1808 absorbed to the analyte particle surfaces. The electronic transitions of many charge transfer complexes are typically in the visible range of the electromagnetic spectrum.

Figure 19:
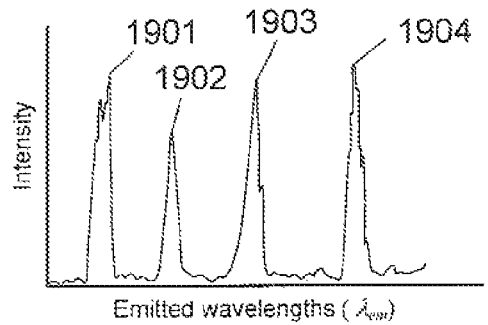
FIG. 19 shows an example Raman spectrum associated with Raman scattered light.

FIG. 19 shows an example Raman spectrum associated with Raman scattered light. The Raman spectrum comprises four intensity peaks 1901-1904, each peak corresponding to a particular wavelength emitted from an excited analyte. The intensity peaks 1901-1904 and associated wavelengths can be used like a finger print to identify the analyte.

The rectangular feature 1802 described above with reference to FIG. 18 represents the operation of only one of the many different types of features described herein. The features described above with reference to FIGS. 2-12 can also be operated in the same manner and can be used to generate a similar enhancement in the intensity of the Raman scattered light emitted by an analyte.

Figure 20:
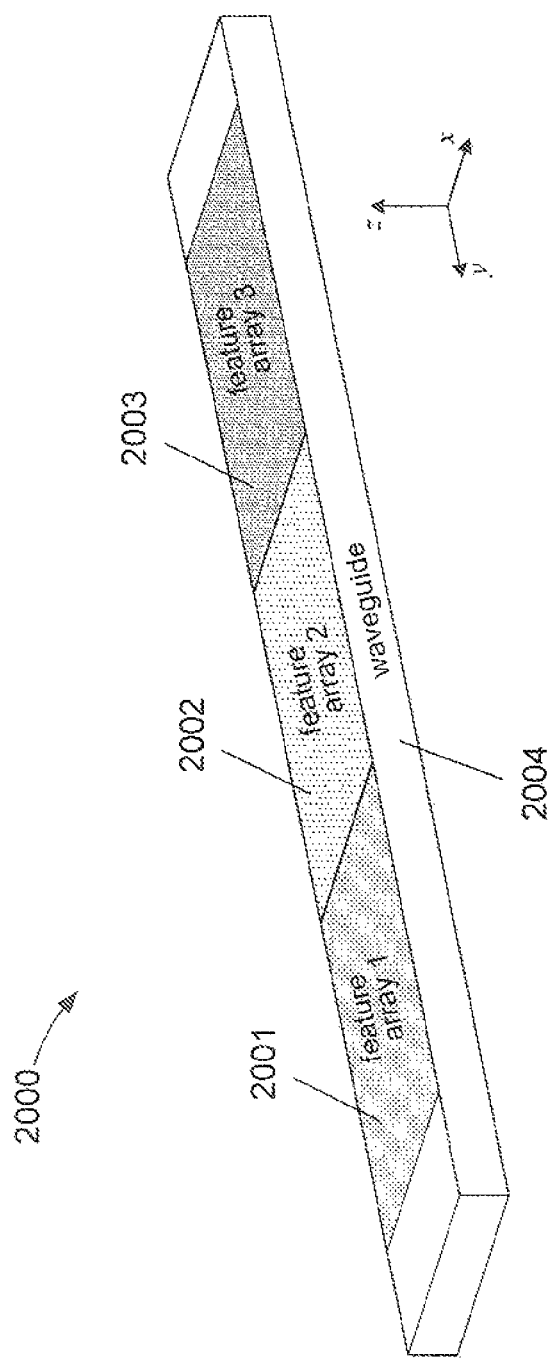
FIG. 20 shows a Raman-active system configured to support guide-mode resonance for three different wavelengths of Raman-excitation light in accordance with embodiments of the present invention.

Raman-active systems are not limited to having a single array of features that support guided-mode resonance for one wavelength of Raman-excitation light. Raman-active system can also be configured with two or more different arrays of features, each array of features configured to support guided-mode resonance with a different wavelength of Raman-excitation light injected into the waveguide. FIG. 20 shows a Raman-active system 2000 configured to support guide-mode resonance for three different wavelengths of Raman-excitation light in accordance with embodiments of the present invention. As shown in the example of FIG. 20, the Raman-active system 2000 is configured with three different arrays of features 2001-2003 formed in a single waveguide 2004. Each array of features can be configured with a different lattice of features as described above with reference to FIGS. 1-12, or each array of features can have the same type of array of features but with different lattice spacing and feature sizes to support different wavelengths. The array of features 2001 can be configured to support Raman-excitation light of a first waveguide, the array of features 2002 can be configured to support Raman-excitation light of a second waveguide, and the array of features 2003 can be configured to support Raman-excitation light of a third waveguide, where the three wavelengths of Raman-excitation light can be injected simultaneously into the waveguide 2004. The waveguide 2000 can be configured as described above with reference to FIGS. 13 through 16.

Figure 21A:
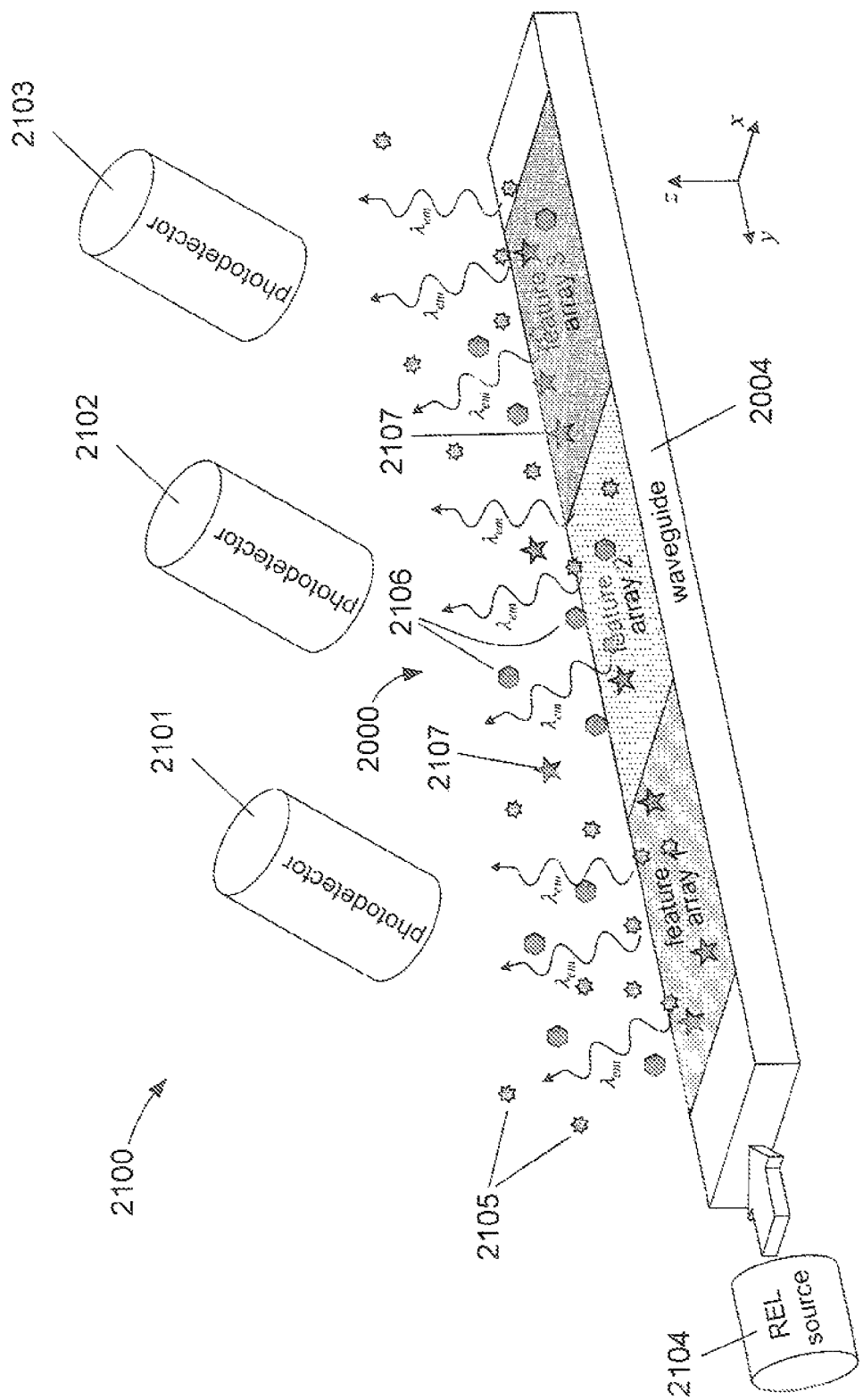
FIGS. 21A-21B shows schematic representations of exemplary analyte sensors configured and operated in accordance with embodiments of the present invention.
Figure 21B:
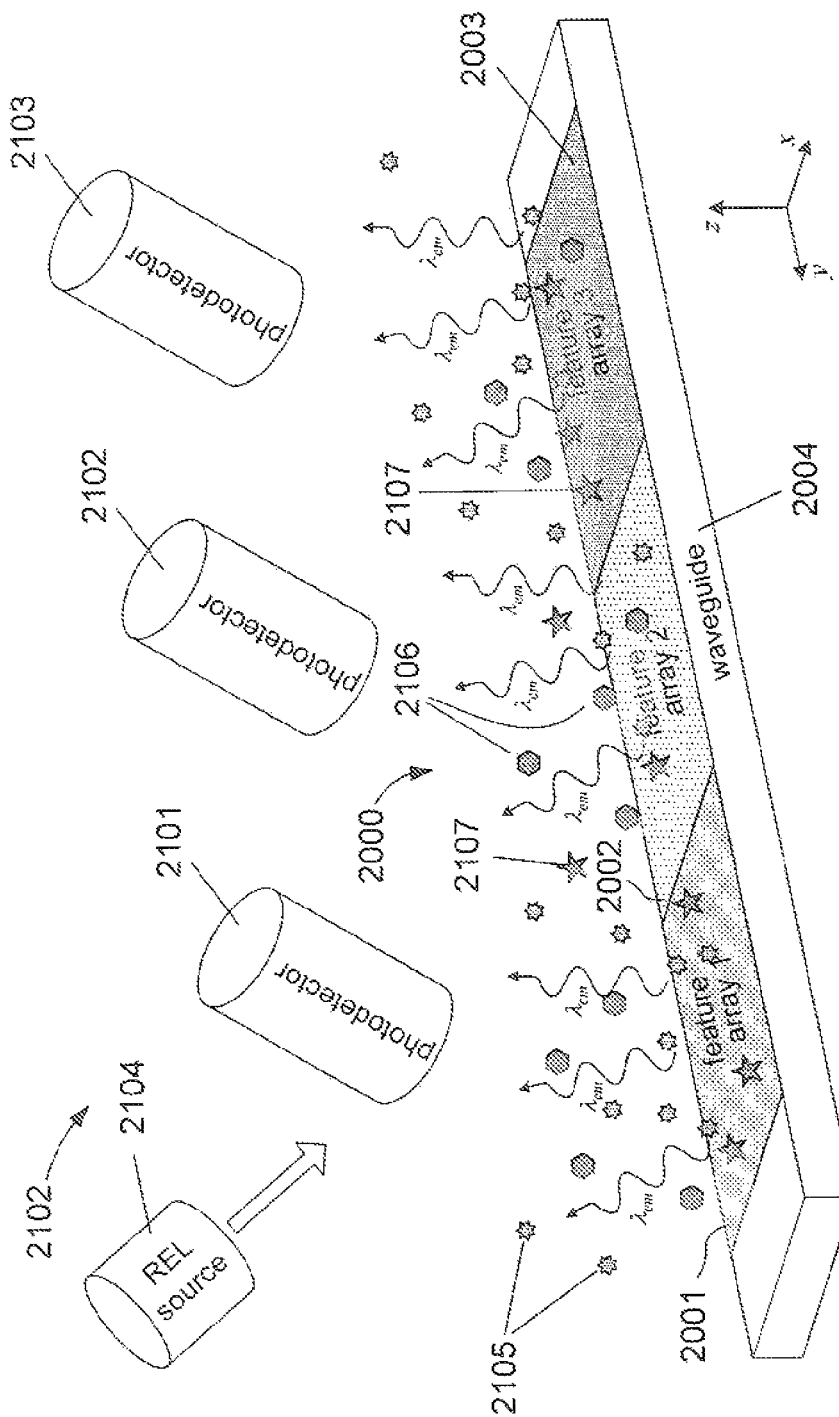

Raman-active systems configured to support guided-mode resonance with two or more wavelengths of Raman-excitation light can be implemented in analyte sensors. FIGS. 21A-21B show schematic representations of exemplary analyte sensors 2100 and 2102, respectively, configured and operated in accordance with embodiments of the present invention. The sensors 2100 and 2102 include the Raman-active system 2000, three photodetectors 2101-2103, and a Raman-excitation light source 2104. Each array of features 2001-2003 supports guided-mode resonance with one of the wavelengths of Raman-excitation light, and each wavelength causes the emission of Raman scattered light from one of the analytes 2105-2107. Photodetectors 2101-2103 are positioned to detect Raman scattered light emitted from three different analytes 2105-2107 located in close proximity to the arrays of features 2001-2003, respectively. As shown in the example of FIG. 21A, the light source 2104 injects three wavelengths of Raman-excitation light into the waveguide layer 2004. As shown in the example of FIG. 21B, the light source 2104 is positioned so that the three wavelengths of Raman-excitation light are directly incident on the arrays of features 2001-2003.

The foregoing description, for purposes of explanation, used specific nomenclature to provide a thorough understanding of the invention. However, it will be apparent to one skilled in the art that the specific details are not required in order to practice the invention. The foregoing descriptions of specific embodiments of the present invention are presented for purposes of illustration and description. They are not intended to be exhaustive of or to limit the invention to the precise forms disclosed. Obviously, many modifications and variations are possible in view of the above teachings. The embodiments are shown and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents:

The invention claimed is:

1. A system for performing Raman spectroscopy, comprising:
a waveguide layer configured with at least one array of features, each array of features and the waveguide layer configured to provide guided-mode resonance for at least one wavelength of electromagnetic radiation; and a material directly disposed on at least a portion of the features of the at least one array of features, wherein the electromagnetic radiation produces enhanced Raman scattered light from analyte molecules located on or in proximity to the material, wherein the material directly disposed on the at least the portion of the features further comprises gold, silver, copper, or another suitable metal for forming surface plasmon polaritons when illuminated by the electromagnetic radiation.

2. The system of claim 1 wherein the at least one array of features further comprises a lattice of approximately regularly spaced features protruding from the waveguide layer and formed from waveguide layer material.

3. The system of claim 2 wherein the lattice of approximately regularly spaced features further comprises a one-dimensional lattice of features.

4. The system of claim 2 wherein the lattice of approximately regularly spaced features further comprises a two-dimensional lattice of features.

5. The system of claim 1 wherein the at least one array of features further comprises a lattice of approximately regularly spaced features formed within the waveguide layer.

6. The system of claim 5 wherein the lattice of approximately regularly spaced features further comprises a one-dimensional lattice of features.

7. The system of claim 5 wherein the lattice of approximately regularly spaced features further comprises a two-dimensional lattice of features.

8. The system of claim 1 wherein the material directly disposed on the at least the portion of the features of the at least one array of features further comprises nanoparticles.

9. The system of claim 1 wherein the material directly disposed on the at least the portion of the features of the at least one array of features further comprises a layer.

10. The system of claim 1 wherein the waveguide layer includes a tapered region that channels and concentrates Raman-excitation light into the at least one array of features, and wherein the waveguide is surrounded by an air cladding.

11. An analyte sensor, comprising: an electromagnetic radiation source configured to emit a range of wavelengths of electromagnetic radiation;
a system for performing Raman spectroscopy, comprising:
waveguide layer configured with at least one array of features, the at least one array of features and the waveguide layer configured to provide guided-mode resonance for at least one wavelength of electromagnetic radiation, and a material directly disposed on at least a portion of the features, wherein the electromagnetic radiation produces enhanced Raman scattered light from analyte molecules located on or in proximity to the material; and at least one photodetector configured to detect the Raman scattered light, wherein the material directly disposed on the at least the portion of the features further comprises gold, silver, copper, or another suitable metal for forming surface plasmon polaritons when illuminated by the electromagnetic radiation.

12. The sensor of claim 11 wherein the at least one array of features further comprises a lattice of approximately regularly spaced features protruding from the waveguide layer and formed from waveguide layer material.

13. The sensor of claim 11 wherein the at least one array of features further comprises a lattice of approximately regularly spaced features formed within the waveguide layer.

14. The sensor of claim 13 wherein the lattice of approximately regularly spaced features further comprises a one-dimensional lattice of features or a two-dimensional lattice of features.

15. The sensor of claim 11 wherein the material directly disposed on the at least the portion of the features further comprises nanoparticles or a layer.

16. The sensor of claim 11 wherein the waveguide layer includes a tapered region that channels and concentrates Raman-excitation light into the at least one array of features, and wherein the waveguide is surrounded by an air cladding.

* * * * *

UNITED STATES PATENT AND TRADEMARK OFFICE
CERTIFICATE OF CORRECTION

| | | |
|---|---|---|
| PATENT NO. | : 8,780,344 B2 | Page 1 of 1 |
| APPLICATION NO. | : 13/384862 | |
| DATED | : July 15, 2014 | |
| INVENTOR(S) | : Jing Tang et al. | |

It is certified that error appears in the above-identified patent and that said Letters Patent is hereby corrected as shown below:

In The Claim

In column 11, line 32, in Claim 11, before "waveguide" insert -- a --.

Signed and Sealed this
Third Day of February, 2015

Michelle K. Lee
*Deputy Director of the United States Patent and Trademark Office*